United States Patent [19]

Krachler et al.

[11] 4,406,155
[45] Sep. 27, 1983

[54] MEASURING APPARATUS FOR THE DETERMINATION OF THE PARTICULATES CONTENT OF EXHAUST GASES

[75] Inventors: Walter Krachler, Hart b.St. Peter; Bruno Schachner, Graz, both of Austria

[73] Assignee: Hans List, Graz, Austria

[21] Appl. No.: 296,834

[22] Filed: Aug. 27, 1981

[30] Foreign Application Priority Data

Sep. 11, 1980 [AT] Austria ................................. 4584/80

[51] Int. Cl.³ .............................................. G01N 1/22
[52] U.S. Cl. ...................................................... 73/28
[58] Field of Search .................... 73/28, 863.22, 863.23

[56] References Cited

U.S. PATENT DOCUMENTS

| | | | |
|---|---|---|---|
| 3,654,801 | 4/1972 | Keefer et al. | 73/28 |
| 3,817,100 | 6/1974 | Anderson et al. | 73/863.23 |
| 4,245,669 | 1/1981 | Schmidt | 73/863.23 |
| 4,246,788 | 1/1981 | Olin et al. | 73/863.23 |

*Primary Examiner*—Stephen A. Kreitman
*Attorney, Agent, or Firm*—Watson, Cole, Grindle & Watson

[57] ABSTRACT

The particulates content of exhaust gases is determined by a sampling device connected to the exhaust supply line. The particulates in the exhaust gases are deposited onto a gas-permeable filter material and the particulates determined by light reflected from the filter material. A constant differential exhaust gas pressure is maintained and a predetermined sample volume per time unit is metered to the filter material. The total cross-section of the exhaust-gas flow through the measuring device is maintained constant. The sampling is taken in short consecutive intervals at a rate such that the characteristics of dynamic changes in the particulates content of the exhaust gas can be determined.

36 Claims, 18 Drawing Figures

MEASURING APPARATUS FOR THE DETERMINATION OF THE PARTICULATES CONTENT OF EXHAUST GASES

BACKGROUND OF THE INVENTION

This invention relates to a measuring apparatus for the determination of the particulates content, especially the soot content, of combustion gases or exhaust gases, respectively, provided with an exhaust gas supply line to a sampling device, with the sampling device effecting during the passage of the exhaust gases the depositing of particulates, especially soot particulates, onto gas-permeable filter material and with an evaluating arrangement, by means of which the light reflection of the filter material which has been blackened with particulates, especially soot particulates, can be correlated with the particulates and respectively, soot content of the exhaust gases.

DESCRIPTION OF THE PRIOR ART

Such measuring apparatuses which determine the soot content of combustion gases by the filter method, are known. Therein, a specified volume of the exhaust gas to be tested is conducted through a specified area of a filter with exactly defined characteristics. The particulates, as filtered out from the combustion gases, are deposited onto the filter material and will blacken same. The differential of light flux reflection between the blackened and unblackened filter material is then determined by way of a photoelectric measuring head and used as indicating value for the particulates or soot content of the combustion gases.

The known measuring apparatuses permit reliable indication of the soot content of combustion gases during steady-state operation of the internal combustion engine emitting the exhaust gases, yet, due to the construction or the modus of functioning of the sampling device, they are limited to a relatively low sampling frequency and thus not usable for rapidly ensuing dynamic changes in the composition of the combustion gas, e.g., during the accelerating phase of an internal combustion engine.

SUMMARY OF THE INVENTION

It is an object of the present invention, to improve a measuring apparatus of the initially named category in such a manner, that rapid changes in the particulates content of combustion gases may also be detected and evaluated by metrological techniques.

According to the present invention, this is made practicable by providing the sampling device with a regulating system serving to maintain a constant differential in the exhaust gas pressure before and after the gas has passed the sampling device; with a first control system by which a predetermined sample volume per time unit can be metered to the filter material; with a second control system for maintaining, at least approximately constant relative to time, the total cross section available for the exhaust gas flow through the measuring apparatus, and by sampling and depositing of particulates and also by evaluation ensuing continually or, respectively, at least quasi-continually at short consecutive time intervals at such rate that the characteristics of dynamic changes in the particulates or soot content of the combustion gas can be determined with unambiguous results. Due to the regulating system, and due to the first control system which will meter to the filter material a predetermined sample volume per time unit, it will then be possible to keep the exhaust gas quantity conducted through the filter material exactly to a desired value, even at high frequencies. Pulsations in the exhaust gas column, occuring under certain circumstances due to shutting-off and opening of the exhaust-gas supply line being repeated at the cadence of sampling, will be effectively prevented by the second control system providing a constant total cross section for this flow. This arrangement will thus allow attaining of very high measuring frequencies without the sampling process per se interfering with the quantitative throughput of exhaust gas, a such interference could also directly affect the measuring results. The characteristics of dynamic changes in the particulates content of the exhaust gases are thus determinable in a simple manner by metrological techniques.

According to an embodiment of the present invention, the first control system of the sampling device is formed by conserving chambers of exactly defined volume, which are chargeable with exhaust gas at the desired measuring frequency and, in turn, dischargeable through the filter material. In concatenation with the regulating system, the conserving chambers will enable maintaining a sample mass of exact definition.

In this connection, it will furthermore be of advantage if the second control system is provided with at least one control port which, at any moment during the entire sampling, will allow flow from the exhaust gas supply line to the conserving chambers through a cross section which is, at least approximately, constant relative to time. This design of the second control system will, in concatenation with the conserving chambers, ensure in a simple manner pulsation-free sampling from the exhaust gas supply line.

In further modification of this invention, the conserving chambers may be arranged in rotational symmetry within at least one chamber cylinder rotatable about its own axis. This arrangement allows to perform particularly simple sampling at high measuring frequencies. According to an especially preferred modification of this invention, the conserving chambers within the chamber cylinder are constructed as through bores of longitudinal orientation within the chamber cylinder, and provided with outlet ports extending radially to the lateral area of the chamber cylinder. The filter material is wrapped about the periphery of the chamber cylinder over at least a portion corresponding to the angular pitch of the outlet ports at the conserving chambers, and the contents of each conserving chamber are dischargeable through the filter material after charging through the control port has been terminated by the continued rotation of the chamber cylinder. The chamber cylinder is therefore provided with longitudinal bores arranged in rotational symmetry at a predetermined pitch and is driven during sampling by a suitable actuator in such a manner, that the measuring frequency as desired in the particular instance for sampling and evaluation can be realized by way of the conserving chambers which are consecutively charged. Since the control port is so constructed that the cross section of supply flow to the conserving chambers are kept at least approximately constant as to time—this being possible, for instance, by constructing the control port as long bore of a width corresponding, at minimum, to the diameter of the conserving chambers constructed as longitudinal bores, and of a length corresponding to the circumferential pitch of the conserving chambers or an integer multiple thereof—an identical flow cross-section for the exhaust gas will be available at any moment during sampling, so that pressure-caused pulsations, which might in an undeterminable manner affect the filling factor of the conserving chamber, will be avoided with certainty. After charging of the individual conserving chambers has been completed the exhaust gas quantity contained therein is discharged via a pressure-differential device operating independently of the introduction of the exhaust gas sample into the conserving chamber and passed through the filter material wrapped about the lateral area of the chamber cylinder.

For this discharging a special suction device may be provided which, according to a further modification of the present invention, is constructed with a housing covering the chamber cylinder at least in the zone where the filter material is wrapped about the cylinder, thus forming an enclosure sealed against the filter material and the chamber cylinder and being subjectable to subatmospheric pressure by means of a vacuum pump. It is also readily practicable within the scope of this invention to use a different method for transporting the exhaust-gas mass contained in the conserving chambers through the filter material, e.g. by raising the pressure of the medium flowing into the chambers subsequent to their discharging.

In order to ensure that no exhaust gas can escape through the outlet ports during sampling and continued rotation of the filled conserving chambers and thus blackened the filter prematurely, provision is made, according to a further proposition of the present invention, for shut-off devices at the conserving chambers, so that the outlet ports for the flow toward the lateral area of the chamber cylinder will be opened only within a predetermined portion of the rotational angle of the respective conserving chamber. Discharging of the sample volume enclosed within the conserving chambers will thus ensue only after completion of sampling and so ensure that the degree of blackening on the filter material will be truly reflective of an exhaust gas quantity being of identical volume at any time.

According to an advantageous embodiment of the present invention, the shut-off devices may be provided with one respective sprin-loaded valve stem having a blind bore and located in the outlet port with a sealing fit and axially displaceable. This valve stem is operable by the tension of the filter material acting over a cross bar and connecting, by means of a cross bore and when filter material is wrapped about, the conserving chamber to the blind bore ending at the filter material. In this case, the tension of the wrapped-about filter material itself will operate the shut-off device sealing the outlet port of the chamber and appropriate arrangement of the control port and the angle of wrap of the, e.g. ribbon-shaped filter material about the conserving chamber will ensure that subsequent to charging the conserving chamber discharge thereof can be effected only within a predetermined zone.

According to a further proposition it is also practicable in this context to have the shut-off devices in the form of spring-loaded sleeve valves supported concentrically and axially displaceable within the conserving chambers. The sleeve valves project beyond a face area of the chamber cylinder and are displaceable against the spring force by an actuating guide arranged external to the chamber cylinder. This will achieve the same effect, however, in this instance independent of the filter material wrapped about the chamber cylinder, thus allowing higher accuracy in controlling the outlet ports in certain instances.

According to a particularly advantageous embodiment of the present invention, provision is made for a scavenging arrangement in the sampling device, whereby, upon the sample discharging from the conserving chambers, the chambers may be scavenged with a purging medium, preferably fresh air. It is thus ensured that upon a sample discharging from the conserving chamber the entire quantity of exhaust gas as previously introduced into the conserving chamber will discharge through the filter material and the conserving chamber will be concomitantly scavenged for again accepting an exhaust-gas sample. It will be of particular advantage therein if, according to a further feature of this invention, the scavenging arrangement be provided with at least one inlet port which will simultaneously coincide with the ports of a plurality of respective adjacent conserving chambers. Discharging of the conserving chambers or scavenging them with fresh air may thus ensue over a portion of the rotational angle depending upon the construction of the inlet ports of the scavenging arrangement, and this will permit holding low the pressure differential required for discharging the sample through the filter material, so that lifting of the filter material away from the periphery of the chamber cylinder is averted with certainty.

According to a further embodiment of the present invention, the sampling device is provided with a dispensing wheel rotatably supported parallel to the axis of the chamber cylinder and sealing with at least a portion of one of its face sides at least a portion of the face side of the chamber cylinder. The dispensing wheel has measuring chambers arranged in rotational symmetry about its axis, which are open toward that face side abutting the chamber cylinder whilst, during rotation of chamber cylinder and dispensing wheel effected by a common drive, the outlet ports of a predetermined number of conserving chambers are in communication with a commensurate number of measuring chambers over a predetermined portion of the angle of rotation which have ports connecting to the lateral area of the dispensing wheel, through which, during coincidence of measuring chambers and discharge ports, exhaust gas from the conserving chambers is dischargeable by a discharging device onto the filter material wrapped about the lateral area of the dispensing wheel. The inlet ports of the conserving chambers are in communication with at least one fresh-air port within this portion of the rotational angle. In this embodiment the sample volume introduced into the conserving chambers of the chamber cylinder in a manner similar to that of the embodiment discussed afore will be transferred within a predetermined portion of the rotational angle into measuring chambers in the dispensing wheel, from where, angle in a manner similar to that of the embodiment discussed afore, it is discharged onto the filter material which is wrapped about the dispensing wheel.

According to a particularly preferred embodiment of the present invention, the pitch circle diameter and also the number of outlet port of the chamber cylinder are constructed at one half of, respectively, the pitch circle diameter and the number of measuring chambers in the dispensing wheel. The chamber cylinder is driven therein at twice the rotational speed of the dispensing wheel, the axes of dispensing wheel and chamber cylinder are in parallel arrangement but offset by one half of the pitch circle diameter of the outlet ports of the chamber cylinder, and the outlet ports are of circular cross-section, and the measuring chambers in the shape of a long bore extending in the radial direction. The width of the long bore at least approximates the diameter of the outlet ports and its length approximately corresponds to the extent of coincidence covered in the radial direction during cooperative action with the outlet ports. By this special geometry, the center of an outlet port of the chamber cylinder will, at any time, be displaced along a diameter of the dispensing wheel, such diameter being simultaneously the longitudinal axis of the respectively appurtenant long-bore-shaped measuring chamber in the dispensing wheel. This will result in partial or full coincidence of an outlet port and a measuring chamber along the abutting area of dispensing wheel and conserving cylinder ensuing for a longer period for discharge of the exhaust gas sample and introduction of fresh air into the conserving and measuring chambers.

According to a still further embodiment of this invention, provision is made for the first control system of the sampling device to include an arrangement for the exact regulation of the feed rate of the filter material, which is continually and for the entire duration of measuring, moved past between an outlet port and a measuring port of known cross-section located in the exhaust gas line, and for a second control system to be combined with the pressure-differential regulating system in such a manner that, prior to passing the measuring port, the filter material is moved past a reference port so that the differential of pressures before and after the filter material is thus determinable. An occasionally different consistency of the filter material, which would be equivalent to a change in the respective flow cross-section and result in a change of the measured pressure differential, may be compensated by effecting variations in parameters of the measurement. Such compensation may, for instance, ensue by at least one of the measured pressures being varied by an adjusting device to conform to the set value, or by direct correction of the measuring results by metrological techniques. This embodiment makes possible continual measuring of the particulates and, respectively, soot content of exhaust gases, for instance during the accelerating phase of the internal combustion engine. The filter material being moved past the measuring port will thus not show individual blackened points but a continuous line having loci of different degrees of blackening. In order to simplify timewise correlation of the measured values it is also possible to affix related reference marks on the filter material, e.g. to time or to a certain reference angle at which the crankshaft of the internal combustion engine is then positioned or to a similar reference.

A still further embodiment of the present invention is characterized by the first control system of the sampling device being combined with the regulating system for the pressure differential, by the second control system comprising two channel cylinders arranged rotatably and parallel to each other on tubular axles in communication with the exhaust gas supply line and the exhaust gas discharge line. The channel cylinders consist, at least on their lateral area, of elastically deformable material and are provided with a respective number of radially outward leading channels and positioned at such distance to each other, that their elastic surfaces are in contact over a zone corresponding in its width at least approximately to the circumferential pitch which is identical for both channel cylinders, of the channel ports. The hollow axles have inlet and outlet ports which will connect to the internal space of the hollow axles only such channels abutting with the porting zone on the lateral area of the respective channel cylinder against the other channel cylinder.

The filter material is movable between the channel cylinders at a rate corresponding to the peripheral speed thereof. The deformable surface of both channel cylinders will thus define a zone between the latters which, with the filter material being interposed therein, will form a continuous gastight channel for the flow of the exhaust-gas sample. Individual blackened zones matching the shape of the channel ports will form on the, for instance ribbon-shaped filter material and be characteristic for the particulates content of the exhaust gases during the period when two respective channels cooperate in a gas-tight manner.

In a further modification of the present invention, it is also practicable so to regulate the pressure differential by means of the first control system, that at any measuring frequency the desired exhaust gas volume can be put through in the period when two channels, with the filter material interposed, will form a gastight connection between the hollow axles.

According to a still further embodiment of the present invention, the first control system is provided with a measuring port connected to the exhaust-gas supply line and with a discharge port connected to an exhaust-gas discharge line, with the filter material being movable between the aforesaid ports, and further provided also with a sequencing arrangement by which at least one of these ports may be lifted from the surface of the filter material whilst the latter is moving forward in steps, the second control system being combined herein with the regulating device for the pressure differential. It will be of advantage in this context if the sequencing arrangement is provided with a cam synchronized with the filter-material feed, which cam will lift only the measuring port away from the filter material. This measuring apparatus, too, will allow obtaining individual blackened zones on the filter material, with the measuring frequency controllable by the operation of the sequencing arrangement or, respectively, by the feed rate of the filter material.

According to a still further feature of this invention, provision may also be made for the measuring port in the exhaust-gas supply line to be enclosed by an annular suction aperture. This will enable precluding to a high degree interference by intake air laterally flowing in whilst the exhaust gas is being conducted through the filter material. A pressure differential will be generated within the additional annular suction aperture, and will draw off the air flowing in and a negligible quantity of exhaust gas, thus ensuring that only highly undiluted exhaust gas will be conducted through the filter.

In order to prevent interference with the measuring results by exhaust gas vapors condensing in the sampling device during sampling, provision is made according to a yet further modification of the present invention for a thermostatic arrangement to keep the sampling device at a temperature above the dew point of the vapors in the exhaust gas.

DESCRIPTION OF THE DRAWINGS

The invention will be explained more closely below with reference to the embodiments represented in the enclosed drawings, wherein.

DESCRIPTION OF THE PREFERRED EMBODIMENTS

Figure 1:
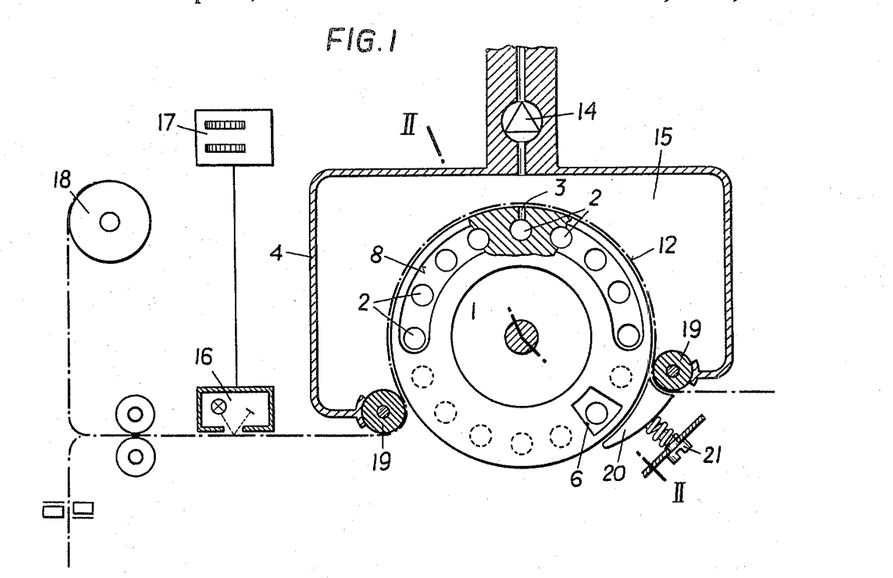
FIG. 1 shows an embodiment of the present invention in a partial schematic view, FIG. 2 a sectional view along line II—II of FIG. 1 on enlarged scale, FIGS. 3a and b a partial section through the chamber cylinder of a different embodiment according to the present invention, FIGS. 4a and b on the left-hand side a section along line IVa—IVa of FIG. 3, and on the right-hand side a section along line IVb—IVb of FIG. 3, FIG. 5 a section according to FIG. 2 through a different embodiment of the present invention, FIG. 6 a detail of the actuating guide in the embodiment according to FIG. 5, FIG. 7 a section through a further embodiment of the present invention, FIG. 8 a schematic view in the direction of arrow VIII in FIG. 7, FIG. 9 a representation of the head plate of FIG. 7, FIG. 10 in a schematic view a further embodiment according to the present invention, FIG. 11 a strip of filter material obtained by a measurement taken with a measuring apparatus according to FIG. 10, FIG. 12 a different embodiment in a schematic view, FIG. 13 an embodiment of the measuring head according to the invention and corresponding to FIGS. 10 and 12, FIG. 14 a further embodiment of the present invention, FIG. 15 a sectional view along line XV—XV in FIG. 14, and FIG. 16 a still further embodiment of the present invention.

The measuring apparatus represented in FIG. 1 comprises in essence a chamber cylinder 1 within which a number of conserving chambers 2 are arranged concentrical to the axis of rotation. The conserving chambers 2 within chamber cylinder 1 are constructed as through bores in its longitudinal orientation, and open at both face sides of chamber cylinder 1. The conserving chambers 2 are, furthermore, provided with one respective outlet port 3 leading radially to the lateral area of chamber cylinder 1. The chamber cylinder 1 is—as can be seen from FIG. 2—sealed at its face sides by sealing discs 5 within a housing 4 and rotatably supported therein. The sealing discs 5 are provided with a control port 6 for the connection of an exhaust-gas supply line 7, a port 10 for the connection of a suction line 11 to aspirate through the exhaust gas, and with one respective inlet port 8, 9 for the scavenging of conserving chamber 2 with fresh air. Ribbon-shaped filter material 12 is wrapped about a portion of the periphery of chamber cylinder 1, fed by a supply roll (not shown) and pressed against the periphery of chamber cylinder 1 by suitable means, such as for instance the hold-down straps 13 shown in FIG. 2.

The stationary guide ribs for directing the exhaust gas in the inlet and outlet ports 6 and 10, are so arranged that upon rotation of chamber cylinder 1 there will always be available a constant cross section for the exhaust gas flowing through the chamber cylinder, so that pulsations in the exhaust gas flow during sampling are avoided. The pressure differential required for the flow of exhaust gas through chamber cylinder 1 is generated by means of a pump (not shown herein) or by other appropriate measures in the exhaust gas line.

The throughput of volume per time unit is so selected herein that charging of conserving chambers 2 is representative for the duration of sampling which, in turn, depends upon the shape of control port 6 and the rotational speed of chamber cylinder 1. The inlet ports 8, 9 for fresh air are so constructed that the aspiration of exhaust gas through the filter material 12 will ensue over a period longer, and a rotational angle of chamber cylinder 1 greater than obtaining in the instance of exhaust gas withdrawal effected through control port 6 from supply line 7. This will allow in a favorable manner keeping low the subatmospheric pressure generated by pump 14 within the internal space 15 of housing 4 for aspirating of samples from conserving chambers 2, and thus prevent lifting of filter material 12 away from the surface of the chamber cylinder.

Since during aspirating of the exhaust gas samples contained in conserving chambers 2, the conserving chambers themselves are in connection with fresh air through ports 8, 9, this will ensure that the entire exhaust gas supplied through exhaust-gas supply line 7 is scavenged out of the respective conserving chambers 2.

The sampling frequency may, in the arrangement as described herein, be varied by suitable selection of rotational speeds of chamber cylinder 1, as well as by selecting suitable pressure differentials in the exhaust gas line and suitable subamospheric pressure, such pressure variations being attainable by suitably adjusting pump 14.

The ribbon-shaped filter material 12 which is blackened after passing housing 4 at the loci cooperating with outlet ports 3, is led to an evaluating arrangement 16, within which the light reflection of the filter material blackened by soot or other particulates is correlated to the particulates content of the combustion gases, and such content is indicated in an indicating device 17.

The already evaluated filter material 12 may, after having passed the evaluation arrangement 16—as shown by the thick line—be conducted out of the apparatus or—as shown by the thin line—be reeled onto a collector spool 18.

Figure 2:
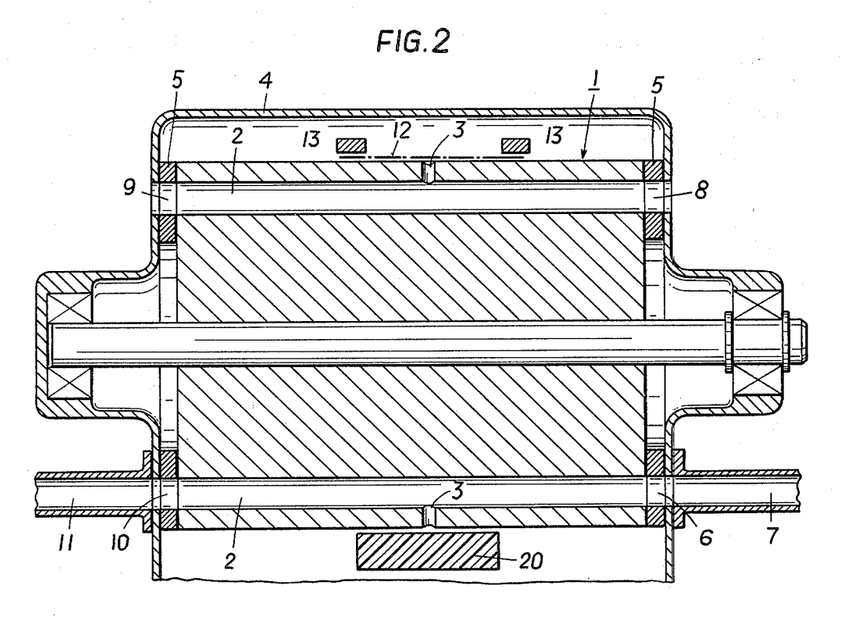

Sealing of housing 4 against chamber cylinder 1 and filter material 12 is effected in the embodiment represented here by means of rolls 19 pressing the filter material 12 onto the peripheral surface of chamber cylinder 1 and also by the use of retainers 20 to seal the gap between chamber cylinder 1, filter material 12 and roll 19 or housing 4, respectively, by means of a spring-loaded screw 21.

Functioning of the arrangement shown in FIGS. 1 and 2 is described hereunder in a simplified manner: The chamber cylinder 1 rotates relative to the sealed housing 4 at a predetermined speed with a given measuring frequency resulting by the circumferential pitch of the conserving chambers 2 at the chamber cylinder. Upon passing control port 6 the conserving chambers 2 are charged through exhaust gas supply line 7 and by means of a device (not shown herein) for generating a constant differential in pressure before and after the gas has passed the sampling device, the exhaust gas reflecting the operating condition of the internal combustion engine at the respective moment. Control ports 6 are so constructed herein that a constant flow cross-section into the conserving chambers is available at all times and the charging time of the chambers is as short as possible. With chamber cylinder 6 rotating on conserving chambers 2 are shut by means of sealing discs 5, whereby the exhaust gas contained within the conserving chambers 2 is isolated from the environment. As soon as the conserving chambers 2 have reached ports 8 and 9, the subatmospheric pressure prevailing in the internal space 15 of housing 4 will become effective and the exhaust gas contained in conserving chambers 2 will be aspirated through radial ports 3 and the filter material 12 wrapped about within this zone.

The blackening on filter material 12 which results in this manner and corresponds in spatial extent to the orifices of outlet ports 3, is evaluated by the aforedescribed method in the evaluating arrangement 16.

Figure 3A:
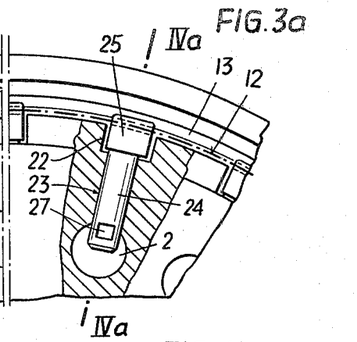
Figure 3B:
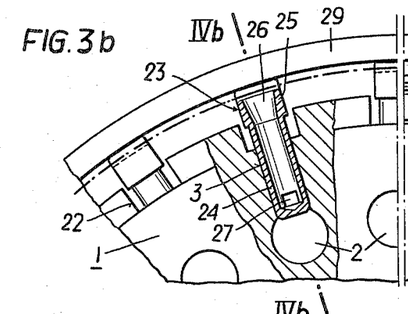
Figure 4A:
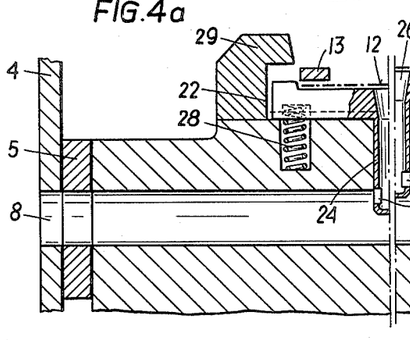
Figure 4B:
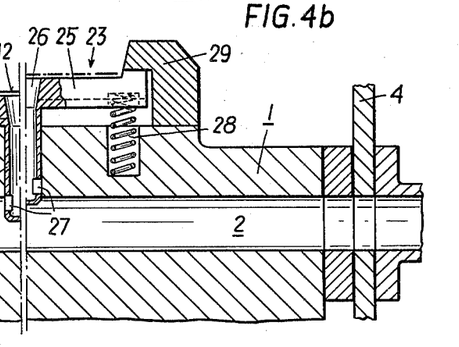

FIGS. 3 and 4 show a practicable construction of an additional shut-off device for outlet ports 3 of each conserving chamber 2. Provision is made therein at the periphery of chamber cylinder 1 for grooves 22 serving conjointly with outlet port 3 to accommodate sliding valves 23. Each sliding valve 23 consists of a valve stem 24 axially displaceable located with a sealing fit within outlet port 3, and a cross bar 25, serving to actuate the valve stem 24 connected to the latter. A blind bore 26 is provided within valve stem 24 and is connected through a lateral bore 27 to the periphery of valve stem 24. By means of springs 28 acting upon cross bars 25 and retainer rings 29 it is ensured that the sliding valve remains closed when in non-actuated state. This state is depicted on the right-hand side of FIG. 4. Upon the ribbon-shaped filter material 12 running up, cross bar 25 is pressed downward against the force of springs 28, as shown in the left-hand side of FIG. 4, and a connection is effected through lateral bores 27 between conserving chamber 2 and blind bore 26 within valve stem 24 which is sealingly fitted into outlet port 3. The exhaust gas contained within conserving chambers 2 may thus be aspirated through the filter material 12 as already discussed with reference to FIGS. 1 and 2.

Figure 5:
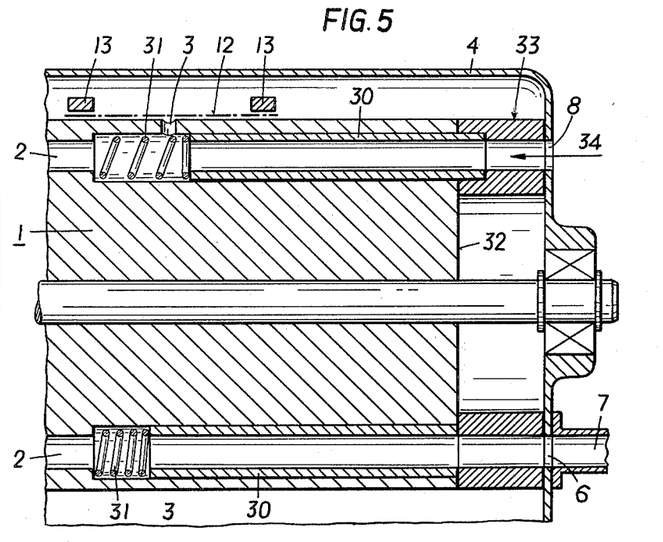
Figure 6:
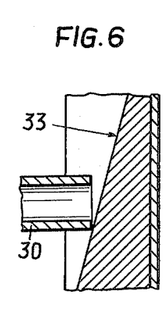

A further practicable construction of a shut-off device for the outlet ports is represented in FIGS. 5 and 6. Provision is made within conserving chambers 2 for tubular sliding valves 30 arranged concentrical to the axis of the conserving chambers; said tubular valves are axially displaceable, have a sealing fit and are loaded by springs 3. The tubular sliding valves 30 project beyond the face area 32 of the chamber cylinder and are operated by an appropriately shaped actuating guide 33 in such a way that upon the conserving chambers 2 being charged with exhaust gas they will close outlet port 3—as shown in the lower part of FIG. 5—and will open outlet ports 3 during discharging of exhaust gas from the conserving chambers 2, i.e. whilst fresh air is subsequently flowing in through port 8 along arrow 34. Appropriate shaping of actuating guide 33 will allow to vary actuation of tubular sliding valves 30 within wide limits.

Figure 7:
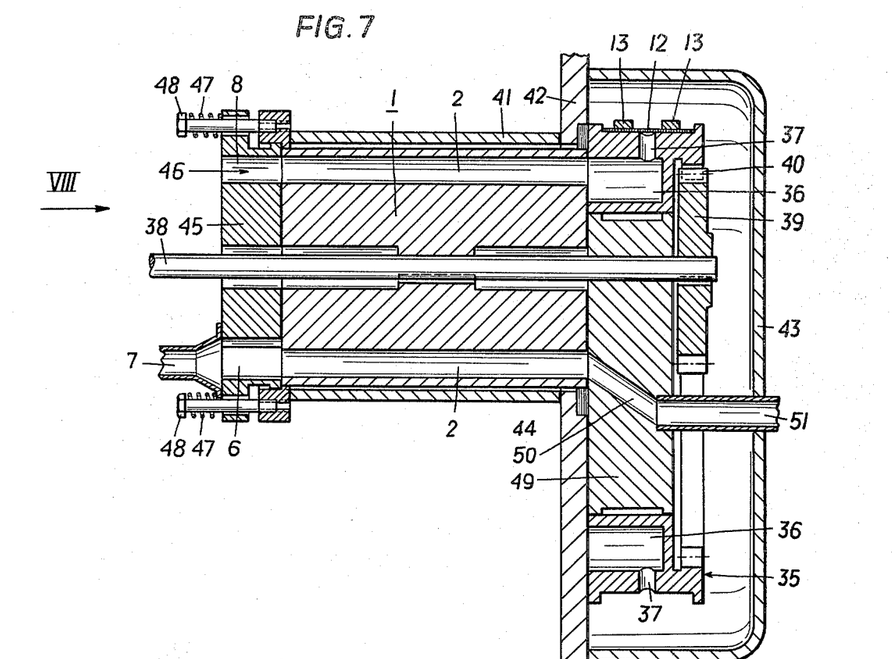
Figure 8:
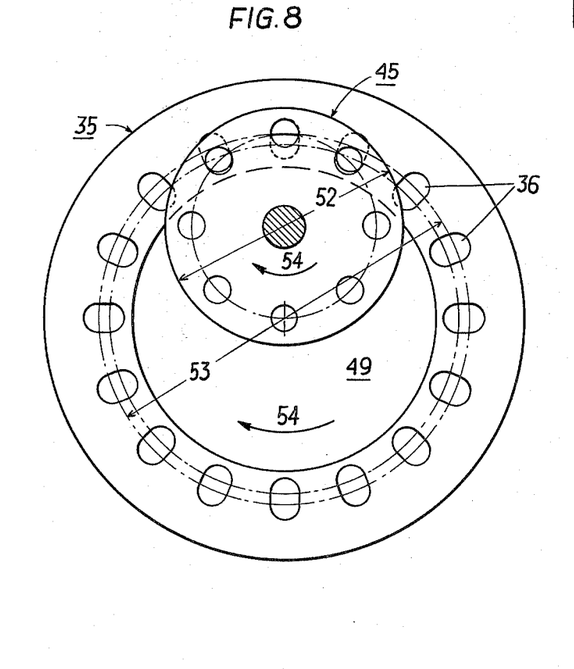
Figure 9:
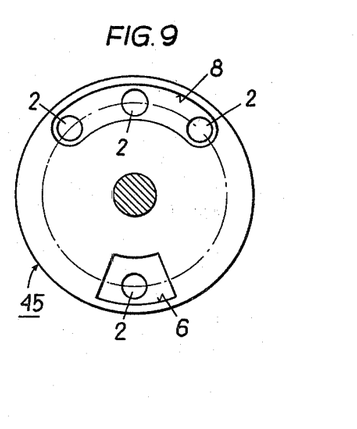

The embodiment shown in FIGS. 7 to 9 is provided, in addition to chamber cylinder 1 which herein again has a number of parallel and concentrically arranged conserving chambers 2, also with a dispensing wheel 35 which is rotatably arranged parallel to chamber cylinder 1 and sealingly abutting with a portion of its face side a portion of the face side of chamber cylinder 1. Dispensing wheel 35 is provided with a number of measuring chambers 36 arranged in rotational symmetry about its axis, open toward that face side of the dispensing wheel which abuts chamber cylinder 1, and having connecting ports 37 to the lateral area of the dispensing wheel.

A shaft 38 drives chamber cylinder 1 and a gear 39 which, in turn, drives dispensing wheel 35 through gearing 40.

The chamber cylinder 1 is enclosed by a housing part 41 attached, in a manner not shown, to a housing plate 42. At the side of the housing plate 42 opposite to the housing part 41 the dispensing wheel 35 including its drive are enclosed by a cover 43 in the internal space of which a subatmospheric pressure is produceable in a manner not shown herein. A gasket 44 is provided for sealing against the space enclosed by the housing part 41.

The chamber cylinder 1 is covered at the face side opposite the dispensing wheel 35 by a head plate 45 which, as shown in FIG. 9, is provided with a control port 6 for the supply of exhaust gas through an exhaust-gas supply line 7 and with an inlet port 8 for fresh air to be supplied in the direction of arrow 46. The head plate 45 is pressed against the face area of chamber cylinder 1 by means of spring 47 which is compressed by screws 48.

The control port 6 in the head plate 45 is again so constructed that an identical cross section for the charging flow to conserving chambers 2 will be available at any position of the rotational angle of chamber cylinder 1; a full respective cross section of conserving chambers 2 will at any time be available since the lateral delimitation of control port 6 corresponds to the circumferential pitch of conserving chambers 2. This also applies in a similar manner with respect to inlet port 8 for fresh air; this port being constructed in the shape of a long bore and also continually coincides with a plurality of conserving chambers 2.

Furthermore, a bearing component 49 is installed on housing plate 42 and the dispensing wheel 35 is supported at the periphery of this bearing component which is also provided with a bore 50 and a subsequently arranged suction line 51 through which the constant pressure differential required for charging the conserving chambers 2 with exhaust gas is produceable.

The pitch-circle diameter 52 as well as the number of outlet ports from the conserving chambers 2 of the chamber cylinder 1 are respectively dimensioned at one half of the outer pitch-circle diameter 53 or, one half of the number of measuring chambers 36 at the dispensing wheel 35. The chamber cylinder 1 is driven at twice the rotational speed of the dispensing wheel 35, with the axes of dispensing wheel and chamber cylinder arranged in parallel but offset by one half of the pitch-circle diameter of the conserving chambers 2.

The outlet ports of the conserving chambers 2 are, in the embodiment as shown, of the same circular cross section as the conserving chambers 2. The measuring chambers 36 are constructed in the shape of a radially extending longitudinal bore of a width at least approximately the diameter of conserving chambers 2 and of a length corresponding at least approximately to the distance covered in the radial direction during cooperation with the outlet ports of the conserving chambers 2.

Upon rotation of chamber cylinder 1 and dispensing wheel 35 along arrows 54, coincidence between conserving chamber 2 with one respective measuring chamber 36 is obtained through a predetermined portion of the rotational angle, as can be seen from FIG. 8, during which coincidence, as can be seen from FIG. 9, the other end of the respective conserving chambers 2 will cooperate with the fresh-air inlet port 8. The subatmospheric pressure prevailing within cover 43 will, in the zone of the above cooperation, cause the exhaust gas contained in conserving chambers 2 to be aspirated into the measuring chambers 36 and via connecting port 37 through the ribbon-shaped filter material 12 which, here again is held against the periphery of dispensing wheel 35 for instance by the positioning straps 13. In this manner blackening of the filter material commensurate with the soot content of the exhaust gases may again be obtained and correlated with the soot content in an evaluating arrangement (not shown). In this embodiment too, the measuring frequency may be varied simply by changing the rotational speed of chamber cylinder and dispensing wheel.

Figure 10:
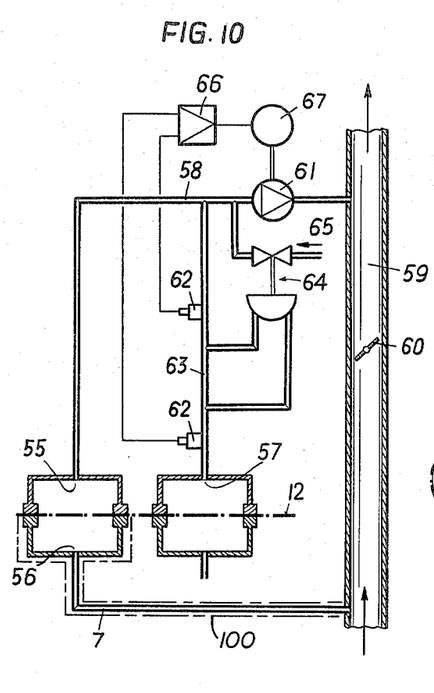

In the embodiment according to FIG. 10 there is provided an arrangement (not shown in the drawing) for the exact regulation of the feed rate of the ribbon-shaped filter material 12, whereby the filter material is continually moved past during the entire measuring period between an outlet port 55 and a measuring port 56 of exactly known cross section which is located in the exhaust gas supply line 7. To regulate the pressure differential between outlet port and measuring port which exerts a direct influence upon the volume per time unit passing through filter material 12, provision is made for a separate reference port 57 past which the filter material 12 is being moved prior to passing measuring port 56. Reference port 57 is connected to exhaust gas line 58 and, at its side opposite to filter material 12, to the free atmosphere.

Figure 11:
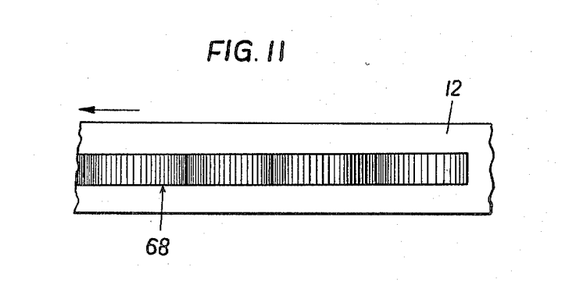

The pressure differential between exhaust gas supply line 7 and discharge line 58, required for the passing of exhaust gas through the filter material, may be produced by a restrictor 60 arranged in the exhaust gas line 59 or by way of a suction pump 61 or also—as shown in FIG. 11—by a combination of both these elements.

Determination of the pressure differential is made herein by using clean and unblackened filter material at the reference port provided for calibrating the filter material, so that irregularities in the filter paper affecting permeability may be compensated. The pressure differential determined, for instance by two suitable pressure transducers 62 at a measuring orifice 63, is used herein as reference value. Regulation of the pressure differential may now ensue either by means of a direct-acting regulating valve 64 which adjusts the pressure differential by allowing a greater or smaller quantity of fresh air to flow in along arrow 65 or by means of a control unit 66 actuated by pressure transducers 62 and acting directly onto the current supply to pump motor 67. FIG. 10 in turn depicts a combination of these capabilities.

Thermostatic device 100 maintains the sampling device at a temperature above the dew point of the vapors in the exhaust gas to prevent condensation of such vapors during sampling and evaluation thereof.

With a continual feed of the ribbon-shaped filter material 12, i.e. by moving past measuring port 56 at a uniform rate, the filter material 12 will, as shown in FIG. 11, be blackened in the shape of a continuous chain of blackened loci 68, wherein timewise correlation of the respective blackening may be facilitated by affixing of reference marks adjacent to the chain of blackened loci (not shown herein).

Figure 12:
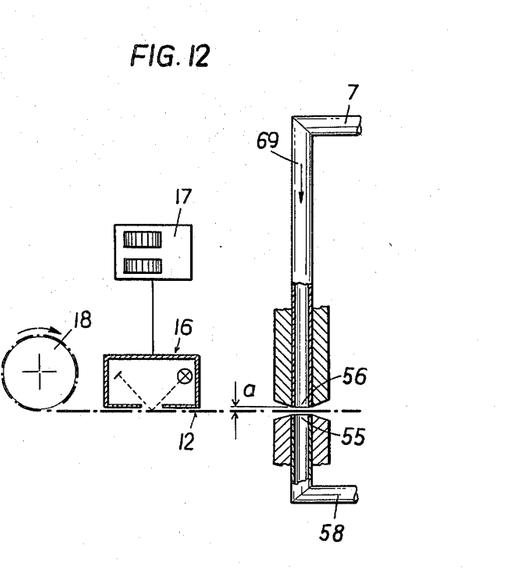

FIG. 12 depicts part of a measuring apparatus similar to that shown in FIG. 10.

The ribbon-shaped filter material 12 is moved at a uniform speed rate between outlet port 55 and measuring port 56 and evaluated in an evaluating arrangement 16 by measuring the change in light reflection, wherein the results of this measurement may be made visible by an indicating device 17 or stored. After the filter material has passed the evaluating arrangement 16 it is reeled onto a collector spool 18.

Upon application of a pressure differential between outlet port 55 and measuring port 56, the filter material 12 will directly rest against the discharge port 55 and thus produce a certain unavoidable gap "a" against measuring port 56. The exhaust gas supplied in the direction of arrow 69 will thus be aspirated through the ribbon-shaped filter material 12 concomitant with an intake-air quantity commensurate with the gap width "a" and is then discharged through exhaust gas discharge line 58.

Figure 13:
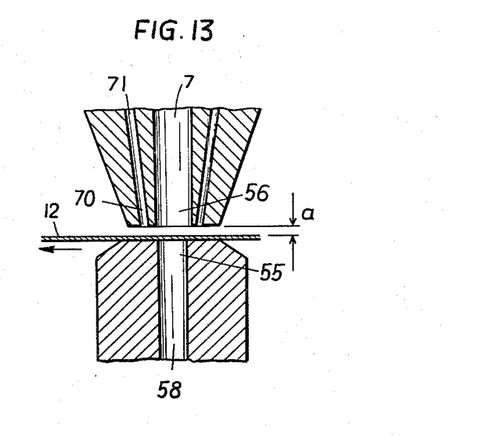

The interference caused by intake air flowing through gap "a", may be compensated for instance by increasing the pressure differential to be commensurate with the dimension of gap "a", this in the manner described with reference to the embodiment of FIG. 10. A further possibility exists, as shown in FIG. 13, by surrounding the measuring port 56 of exhaust gas supply line 7 with an additional annular suction orifice 70 which may be subjected to subatmospheric pressure via a suction passage 71. The measuring port 56 will be of a somewhat greater dimension in its cross section than the cross section of exhaust gas discharge line 58 which governs the spatial extent of blackening upon the filter material 12. A pressure differential is produced in the additional suction orifice 70 aspirating the intake air flowing through gap "a" and also a small quantity of exhaust gas from exhaust gas supply line 7, and it is accomplished thereby that only highly undiluted exhaust gas will permeate the filter material 12 itself.

In both measuring apparatuses shown in FIGS. 10 and 12, it is furthermore practicable within the scope of the invention that in the event of the pressure differential deviating from a set value, it will not be the pressure differential that is adjusted to set value, but the measuring result determined by way of evaluating arrangement 16 will be directly correctable by metrological technique, for instance electronically.

Figure 14:
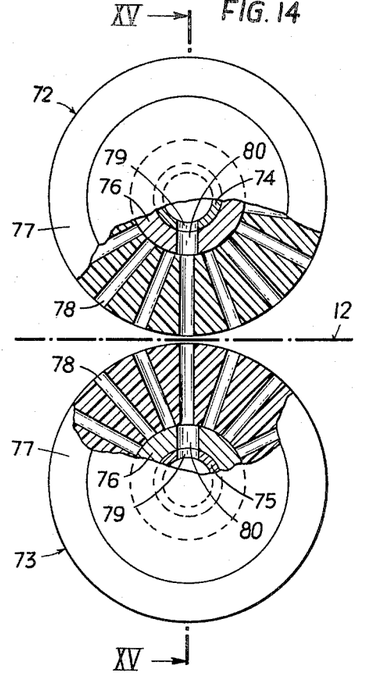
Figure 15:
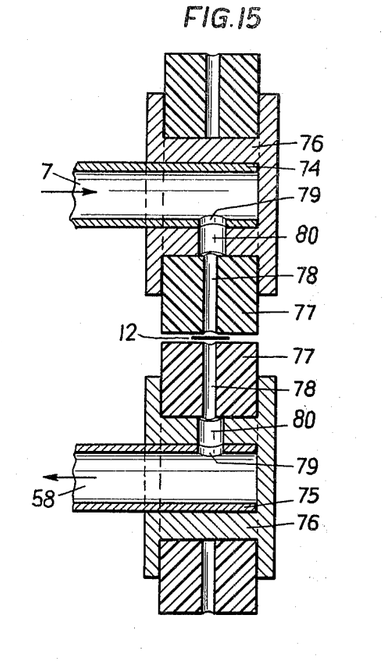

The sampling device of a measuring apparatus according to the present invention and shown in FIGS. 14 and 15 comprises two channel cylinders 72, 73 supported rotatably and parallel to each other on tubular axles 74, 75 which are in communication with exhaust gas supply line 7 and exhaust gas discharge line 58. Channel cylinders 72, 73 are provided with one respective hub part 76 of non-deformable material, carrying at its external area a jacket part 77 of elastically deformable material, in which a number of radially outward oriented channels 78 is provided. Channel cylinders 72, 73 are supported at such distance to each other, that their elastic jacket-parts 77 will be in contact over a zone of a width corresponding, at least approximately, to the peripheral pitch of the ports for channels 78 which is identical for both channel cylinders. The hollow axles 74, 75 have inlet and outlet ports 79 which, cooperating with bores 80 in the hub parts 76, will connect such channels 78 to the interior space of hollow axles 74, 75 only when the respective porting zone of these channels at the lateral area of the respective channel cylinder abuts against the other channel cylinder. The ribbon-shaped filter material 12 is movable between the two channel cylinders 72, 73 at a rate corresponding to their peripheral speed, whereby individual blackened zones commensurate with the port cross-sections of channels 78 will result on the filter material in the zone of elastic abutment of the channel cylinder surfaces. This blackening is then evaluable in the manner already discussed with reference to the abovementioned embodiments.

Figure 16:
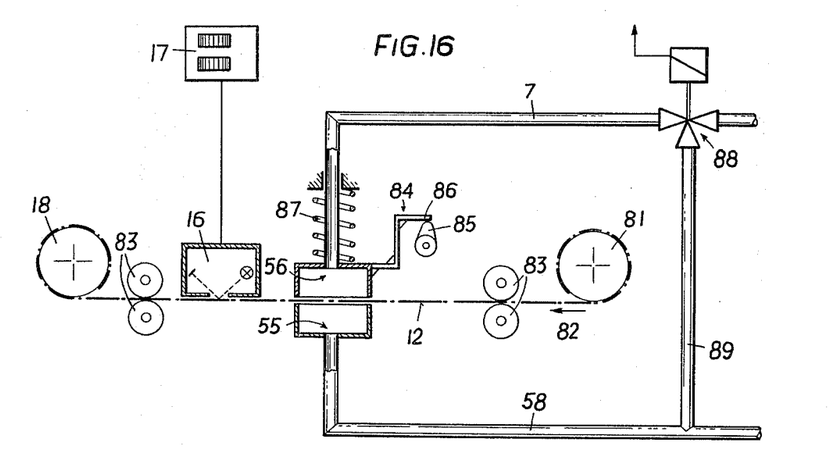

In the measuring apparatus according to FIG. 16 ribbon-shaped filter material 12 is running from a new spool 81, drawn along arrow 82 by rollers 83 and is, after passing the sampling device and the subsequent evaluating arrangement 16, and again drawn by rollers 83, reeled onto the collector spool 18.

Exhaust gas is supplied to the filter material 12 through exhaust gas supply line 7 and measuring port 56, with the pressure differential between exhaust gas supply line 7 and exhaust gas discharge line 58 being regulable herein in a manner not shown. Measuring port 56 is provided with a sequencing arrangement 84 serving to lift the measuring port away from the surface of the filter material 12. This is accomplished by a cam 85 which is synchronized with the filter-material feed in a manner not shown. This cam acts through a linkage 86 and against the effect of a spring 87 to lift the component carrying measuring port 56.

In order to prevent during the transport phase of the filter material 12 that a gas-air mixture is aspirated through the filter material, thus supplying an erroneous measuring signal, it is possible during this time by means of a changeover valve 88 arranged in the exhaust gas supply line 7, to short-circuit the exhaust gas supply line 7 to the exhaust gas discharge line 58 by direct connection through a bypass line 89.

Common to all embodiments discussed herein is the high measuring frequency made possible by arranging the sampling device according to the present invention, so that even rapid changes in exhaust gas composition, as, for instance, occuring during accelerating phases of internal combustion engines, may be detected by metrological techniques.

We claim:

1. Measuring apparatus for the determination of the particulates content of exhaust gases, comprising a sampling device and an exhaust gas supply line connected thereto, with said sampling device effecting during the passage of the exhaust gases the depositing of particulates onto gas-permeable filter material, and an evaluating arrangement by means of which the light reflection of the filter material which has been blackened with particulates is correlated with the particulates content of the exhaust gases, wherein said sampling device comprises a regulating system for maintaining a constant differential in the exhaust gas pressure before and after the gas has passed said sampling device; a first control system by which a predetermined sample volume per time unit is metered to the filter material; and a second control system for maintaining, at least approximately constant relative to time, the total cross section available for the exhaust-gas flow through the measuring apparatus; and wherein the sampling and depositing of particulates and also the evaluation ensues at least quasi-continually in short consecutive intervals at such rate that the characteristics of dynamic changes in the particulates content of the exhaust gas can be determined with unambiguous results.

2. Measuring apparatus according to claim 1, wherein said first control system of said sampling device is formed by conserving chambers of exactly defined volume, said chambers being chargeable with exhaust gas at the desired measuring frequency and, in turn, dischargeable through the filter material.

3. Measuring apparatus according to claim 2, wherein said second control system is provided with at least one control port which, at any moment during the entire sampling, will enable flow from the exhaust gas supply line to the conserving chambers through a total cross-section which, at any moment of sampling will be at least approximately constant as to time.

4. Measuring apparatus according to claim 2 or 3, wherein said conserving chambers are arranged in rotational symmetry within at least one chamber cylinder rotatable about its own axis.

5. Measuring apparatus according to claim 4, wherein said conserving chambers are constructed as through bores of longitudinal orientation within said chamber cylinder, and provided with outlet ports extending radially to the lateral area of said chamber cylinder and the filter material is wrapped about the periphery of said chamber cylinder over at least a portion commensurate with the angular pitch of said outlet ports at said conserving chambers; and wherein the content of each individual conserving chamber is dischargeable through the filter material after charging through said control port has been terminated by the continued rotation of said chamber cylinder.

6. Measuring apparatus according to claim 5, additionally comprising a suction device with a vacuum pump for discharging said conserving chambers, with a housing covering said chamber cylinder at least in the zone where the filter material is wrapped around said cylinder, thus sealing against the filter material and said chamber cylinder, and being subjectable to subatmospheric pressure by means of said vacuum pump.

7. Measuring apparatus according to claim 6, additionally comprising shut-off devices for said conserving chambers to open said outlet ports toward the lateral area of said chamber cylinder only within a predetermined portion of the rotational angle of the respective chamber.

8. Measuring apparatus according to claim 6, further comprising a scavenging arrangement in said sampling device for scavenging said chambers with purging medium upon the sample discharging from said conserving chambers.

9. Measuring apparatus according to claim 8, wherein said shut-off devices being provided with one respective spring-loaded valve stem having a blind bore and located with a sealing fit and axially displaceable in said outlet port, said valve stem being operable by the tension of the filter material acting over a cross bar and connecting, by means of a cross bore and when filter material is wrapped about, said conserving chamber to said blind bore ending at the filter material.

10. Measuring apparatus according to claim 8, wherein said shut-off devices being formed by spring-loaded sleeve valves supported concentrically and axially displaceable within said conserving chambers, said sleeve valves projecting beyond the face side of said chamber cylinder and being displaceable against the spring force by an actuating guide arranged external to said chamber cylinder.

11. Measuring apparatus according to claim 5, additionally comprising shut-off devices for said conserving chambers to open said outlet ports toward the lateral area of said chamber cylinder only within a predetermined portion of the rotational angle of the respective chamber.

12. Measuring apparatus according to claim 11, wherein said shut-off devices being provided with one respective spring-loaded valve stem having a blind bore and located with a sealing fit and axially displaceable in said outlet port, said valve stem being operable by the tension of the filter material acting over a cross bar and connecting, by means of a cross bore and when filter material is wrapped about, said conserving chamber to said blind bore ending at the filter material.

13. Measuring apparatus according to claim 11, wherein said shut-off devices being formed by spring-loaded sleeve valves supported concentrically and axially displaceable within said conserving chambers, said sleeve valves projecting beyond the face side of said chamber cylinder and being displaceable against the spring force by an actuating guide arranged external to said chamber cylinder.

14. Measuring apparatus according to claim 11, further comprising a scavenging arrangement in said sampling device for scavenging said chambers with a purging medium upon the sample discharging from said conserving chambers.

15. Measuring apparatus according to claim 14, wherein said shut-off devices being provided with one respective spring-loaded valve stem having a blind bore and located with a sealing fit and axially displaceable in said outlet port, said valve stem being operable by the tension of the filter material acting over a cross bar and connecting, by means of a cross bore and when filter material is wrapped about, said conserving chamber to said blind bore ending at the filter material.

16. Measuring apparatus according to claim 14, wherein said shut-off devices being formed by spring-loaded sleeve valves supported concentrically and axially displaceable within said conserving chambers, said sleeve valves projecting beyond the face side of said chamber cylinder and being displaceable against the spring force by an actuating guide arranged external to said chamber cylinder.

17. Measuring apparatus according to claim 5, comprising a scavenging arrangement in said sampling device, with at least one inlet port which, in the respective instance will simultaneously coincide with the respective ports of a plurality of adjacent conserving chambers.

18. Measuring apparatus according to claim 5, further comprising a scavenging arrangement in said sampling device for scavenging said chambers with a purging medium upon the sample discharging from said conserving chambers.

19. Measuring apparatus according to claim 18, wherein said shut-off devices being provided with one respective spring-loaded valve stem having a blind bore and located with a sealing fit and axially displaceable in said outlet port, said valve stem being operable by the tension of the filter material acting over a cross bar and connecting, by means of a cross bore and when filter material is wrapped about, said conserving chamber to said blind bore ending at the filter material.

20. Measuring apparatus according to claim 18, wherein said shut-off devices being formed by spring-loaded sleeve valves supported concentrically and axially displaceable within said conserving chambers, said sleeve valves projecting beyond the face side of said chamber cylinder and being displaceable against the spring force by an actuating guide arranged external to said chamber cylinder.

21. Measuring apparatus according to claim 4, wherein said sampling device is provided with a dispensing wheel, rotatably supported parallel to the axis of said chamber cylinder and sealing with at least a portion of one of its face sides at least a portion of the face side of said chamber cylinder, said dispensing wheel having measuring chambers therein arranged in rotational symmetry about its axis and open towards the face side abutting against said chamber cylinder, said outlet ports of a predetermined number of conserving chambers being, during rotation of chamber cylinder and dispensing wheel, effected by a common drive, in communication with a corresponding number of conserving chambers through a predetermined portion of the rotational angle, and wherein said measuring chambers have connecting ports to the lateral area of the dispensing wheel through which, during coincidence of said measuring chambers with said discharge ports, exhaust gas from said conserving chambers is dischargeable by a discharging device through the filter material wrapped about the lateral area of said dispensing wheel, and wherein the inlet ports of said conserving chambers are, within this portion of the rotational angle, in communication with at least one fresh-air port.

22. Measuring apparatus according to claim 21, wherein the pitch circle diameter and also the number of said outlet ports is one half of the pitch circle diameter and the number of measuring chambers of said dispensing wheel, said chamber cylinder is driven at twice the rotational speed of said dispensing wheel, with the axes of said dispensing wheel and said chamber cylinder being in parallel arrangement but offset by one half of the pitch circle diameter of said outlet ports of said chamber cylinder, and wherein said outlet ports are of circular cross section and said measuring chambers are in the shape of a long bore extending in the radial direction, with the width of said long bore at least approximately corresponding to the diameter of said outlet ports and its length approximately corresponding to the extent of coincidence in the radial direction during cooperative action with said outlet ports.

23. Measuring apparatus according to claim 4, further comprising a scavenging arrangement in said sampling device for scavenging said chambers with a purging medium upon the sample discharging from said conserving chambers.

24. Measuring apparatus according to claims 2 or 3, further comprising a scavenging arrangement in said sampling device, by means of which, upon the sample discharging from said conserving chambers, said chambers may be scavenged with a purging medium.

25. Measuring apparatus according to claim 1, wherein said first control system of said sampling device includes an arrangement for the exact regulation of the feed rate of the filter material, said filter material being continually moved past between an outlet port and a measuring port of known cross-section located in said exhaust gas supply line for the entire duration of measuring, said second control system being combined with said pressure-differential regulating system, which additionally comprises a reference port, in such a manner that, prior to passing the measuring port, the filter material is moved past said reference port where the differential of pressures before and after the filter material is determinable, and wherein an occasionally different consistency of the filter material, which would be equivalent to a change in the respective flow cross-section and result in a change of the pressure differential, as measured at said reference port, may be compensated by altering of parameters of the measurement.

26. Measuring apparatus according to claim 25, wherein at least one of the measured pressures is variable by means of an adjusting device in the event of the pressure differential deviating from a desired value.

27. Measuring apparatus according to claim 26, wherein said adjusting device acts upon the power supply of a suction-pump motor.

28. Measuring apparatus according to claim 26, wherein said adjusting device comprises a regulating valve which may be vented to the free atmosphere.

29. Measuring apparatus according to claim 15, further comprising means for measuring the magnitude of the differential pressure, means for detecting the deviation from a desired value, and means for correcting the measured value in accordance with said deviation.

30. Measuring apparatus according to claim 25, further comprising means for detecting said pressure differential, and means for charging said measured value in accordance with said differential pressure.

31. Measuring apparatus according to claim 1, wherein said first control system of said sampling device is combined with said regulating system for the pressure differential; said second control system comprises two channel cylinders arranged rotatably and parallel to each other on tubular axles in communication with said exhaust gas supply line and an exhaust gas discharge line, said channel cylinders consisting, at least on their lateral area, of elastically deformable material and being provided with a respective number of radially outward leading channels; said channel cylinders further being positioned at such distance to each other, that their elastic surfaces are in contact over a zone corresponding in its width at least approximately to the circumferential pitch of said channel ports, said pitch being identical for both channel cylinders, and wherein said hollow axles have inlet and outlet ports allowing in the respective instances connection to the internal space of the hollow axles of only such channels which abut with their porting zone on the lateral area of the respective channel cylinder against the other cylinder, and said filter material being movable between the channel cylinders at a rate corresponding to the peripheral speed thereof.

32. Measuring apparatus according to claim 31, wherein the differential pressure being regulable by said first control system in a manner allowing the desired exhaust-gas quantity to be put through at any desired frequency within the time when two channels, with the filter material interposed, are forming a gas-tight connection between said hollow axles.

33. Measuring apparatus according to claim 1, wherein said first control system is provided with a measuring port connected to said exhaust-gas supply line and with a discharge port connected to an exhaust gas discharge line, with the filter material being movable between the aforesaid ports, and being further provided also with a sequencing arrangement by which at least one of said ports may be lifted from the surface of the filter material as the latter is moving forward in steps, and said second control system being combined with said regulating device for the pressure differential.

34. Measuring apparatus according to claim 33, wherein said sequencing arrangement being provided with a cam synchronized with the filter-material feed, which cam will lift only said measuring port away from the filter material.

35. Measuring apparatus according to claim 25 or 33, wherein said measuring port is surrounded by an annular suction aperture.

36. Measuring apparatus according to claim 1, additionally comprising a thermostatic device for said sampling device, which keeps the latter at a temperature above the dew point of the vapors in the exhaust gas, will prevent condensation of vapors contained in the exhaust gas during sampling and evaluation.

* * * * *